(12) United States Patent
Meiser et al.

(10) Patent No.: US 7,470,396 B2
(45) Date of Patent: Dec. 30, 2008

(54) DEVICE AND METHOD FOR ESTABLISHING AN ARTIFICIAL ISOLATED CIRCULATION IN A TARGET AREA OF A HUMAN OR ANIMAL BODY

(75) Inventors: Andreas Meiser, Bochum (DE); Achim Mumme, Bochum (DE)

(73) Assignee: Jostra AG, Hirrlingen (DE)

( * ) Notice: Subject to any disclaimer, the term of this patent is extended or adjusted under 35 U.S.C. 154(b) by 511 days.

(21) Appl. No.: 10/670,999

(22) Filed: Sep. 25, 2003

(65) Prior Publication Data

US 2005/0101934 A1 May 12, 2005

(30) Foreign Application Priority Data

Sep. 26, 2002 (DE) .................. 102 45 772

(51) Int. Cl.
*A61M 1/00* (2006.01)
*A61M 37/00* (2006.01)
*A61M 5/00* (2006.01)
*A61B 5/08* (2006.01)

(52) U.S. Cl. .................. 422/45; 604/6.14; 422/44; 422/46; 600/531

(58) Field of Classification Search ....... 604/4.01–6.16, 604/65–67, 96.01, 27, 35, 28, 43, 97.01, 604/97.03, 98.01, 101.01–102.03, 171, 192.194; 600/531, 6.14, 96.01; 422/44–48; 606/191–194
See application file for complete search history.

(56) References Cited

U.S. PATENT DOCUMENTS

| 5,614,378 | A | * | 3/1997 | Yang et al. .................. 435/41 |
| 5,957,880 | A | * | 9/1999 | Igo et al. .................. 604/6.11 |
| 6,287,273 | B1 | * | 9/2001 | Allers et al. .................. 604/27 |
| 6,508,777 | B1 | * | 1/2003 | Macoviak et al. .......... 604/4.01 |
| 6,555,058 | B2 | * | 4/2003 | Kamibayashi et al. ........ 422/44 |
| 6,689,315 | B2 | * | 2/2004 | Linker et al. .................. 422/45 |
| 6,699,202 | B1 | * | 3/2004 | Gambert et al. ............. 600/532 |
| 6,827,898 | B1 | * | 12/2004 | Fausset et al. ................ 422/46 |
| 2002/0012988 | A1 | * | 1/2002 | Brasile ..................... 435/284.1 |
| 2002/0085952 | A1 | * | 7/2002 | Ellingboe et al. ............. 422/45 |
| 2003/0095892 | A1 | * | 5/2003 | Patterson et al. ............. 422/45 |
| 2004/0081580 | A1 | * | 4/2004 | Hole et al. .................... 422/44 |

FOREIGN PATENT DOCUMENTS

| DE | 43 10 378 | | 10/1994 |
| FR | 2 558 592 | | 7/1985 |
| WO | WO 01/03755 | | 1/2001 |
| WO | WO 01/43804 | * | 6/2001 |

OTHER PUBLICATIONS

Barker et al.; "Continuous intraoperative external monitoring of perfusiate leak using iodine-131 human serum albumin during isolated perfusion of the liver and limbs"; vol. 22, No. 11; Jun. 7, 1995; Springer Berlin; European Journal of Nuclear Medicine; pp. 1242-1248.*

(Continued)

*Primary Examiner*—Tatyana Zalukaeva
*Assistant Examiner*—Phil Wiest
(74) *Attorney, Agent, or Firm*—Knobbe, Martens, Olson & Bear LLP

(57) ABSTRACT

A device for establishing an isolated perfusion including a pump arrangement, a venous catheter, and an arterial catheter, for establishing an artificial circulation in a target area of a human or animal body, which artificial circulation is isolated from the systemic circulation. The device has first means for feeding an analysis gas into the artificial circulation, and second means for monitoring whether a blood exchange takes place between the artificial circulation and the systemic circulation.

11 Claims, 1 Drawing Sheet

OTHER PUBLICATIONS

"Double-Balloon Catheter for Isolated Liver Perfusion: An Experimental Study" by Cwikiel et al; Cardio Vascular and Interventional Radiology 24 (2001); pp. 191-193.

"Quantitative Radionuclide Leakage Monitoring during Isolated Limb Perfusion" by Sprenger et al; NuklarMedizin 33 (1994); pp. 248-253.

* cited by examiner

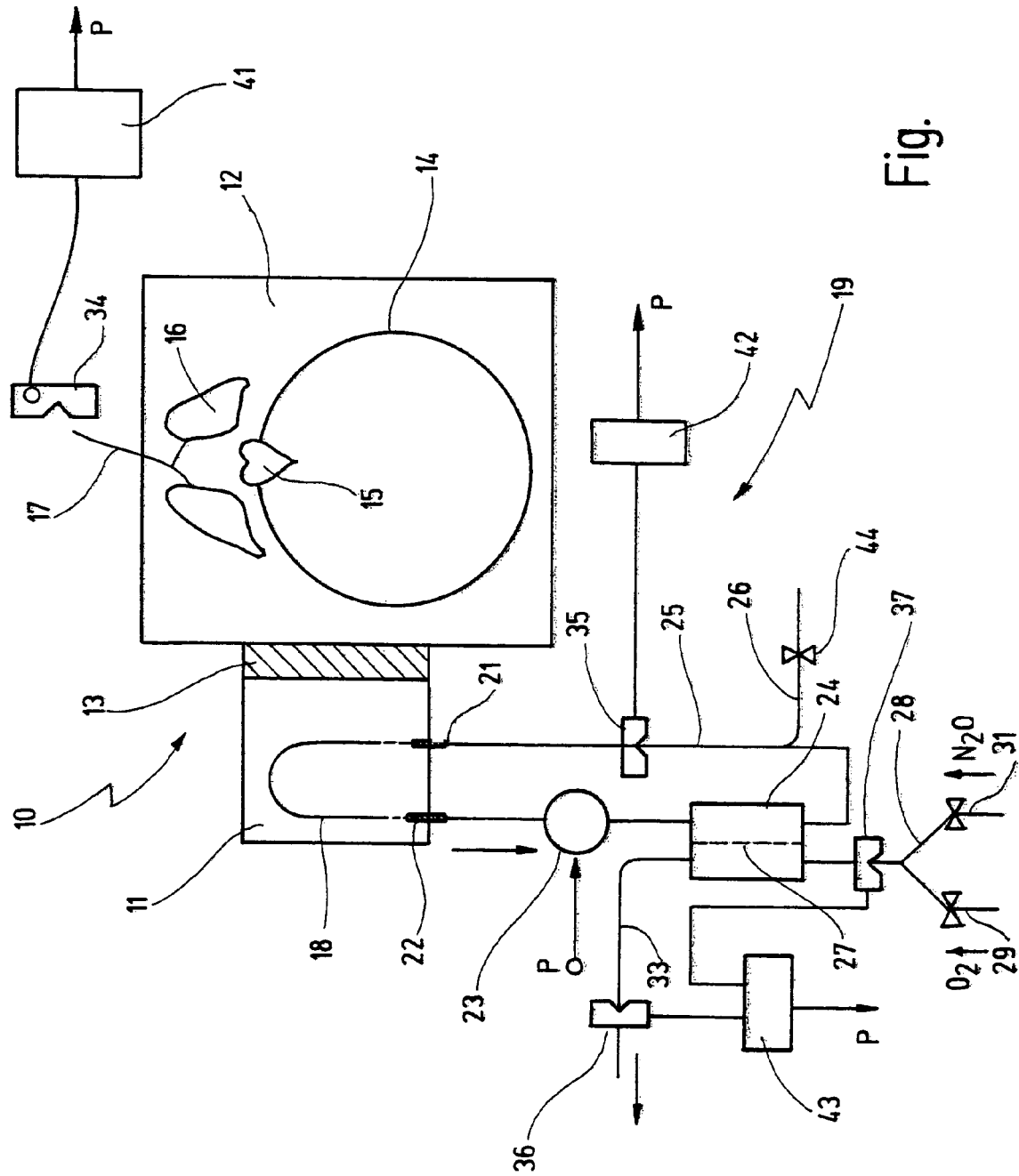
Fig.

DEVICE AND METHOD FOR ESTABLISHING AN ARTIFICIAL ISOLATED CIRCULATION IN A TARGET AREA OF A HUMAN OR ANIMAL BODY

CROSS-REFERENCES TO RELATED APPLICATIONS

This application is claiming priority of copending German patent application DE 102 45 772.7 filed on Sep. 26, 2002, which is incorporated herein by reference.

BACKGROUND OF THE INVENTION

1. Field of the Invention

The present invention relates to a device with a pump arrangement, with at least one venous catheter, and with at least one arterial catheter, for establishing and maintaining an artificial circulation in a target area of a human or animal body, the artificial circulation being isolated from the blood circulation of the body.

The invention further relates to a method in which an artificial circulation is established and maintained in a target area of a human or animal body, said artificial circulation being isolated from the blood circulation of the body, hereinafter also called the systemic circulation.

2. Related Prior Art

This so-called isolated perfusion of organs or body regions has been used for some time to administer powerful medicaments in the target area and in so doing to avoid their side effects on the rest of the organism, or to administer medicaments at such high concentrations which, if applied systemically, would cause unacceptably severe side effects and incompatibility reactions.

In the context of the present invention, the term "target area" means an organ which can be isolated from the rest of the body in terms of blood circulation, or a body region which can be isolated, for example the extremities, i.e. arms or legs, and the pelvis. A prime example is hyperthermic isolated perfusion with chemotherapeutic substances for treating loco-regional metastases in the arms or legs in cases of malignant melanoma. Other examples include pelvic perfusion in local metastasis of rectal carcinoma, or leg perfusion for dissolution of otherwise treatment-resistant leg-vein thrombosis of the legs. An important area of application of the present invention relates to the last-mentioned thrombolytic perfusion of isolated limbs, predominantly the legs.

To carry out the isolated perfusion, use is made of a pump arrangement with at least one venous catheter and with at least one arterial catheter which are connected to the artery and vein of the target area so that, for a certain time, a small artificial circulation is established and maintained which is separate from the rest of the blood circulation. In order to supply the target area with oxygen in cases where the artificial circulation is maintained for a relatively long period, an oxygenator is also coupled into the artificial circulation, and the carbon dioxide level is also kept constant by means of this oxygenator.

Hitherto, the artery and vein of the target area were therefor surgically exposed, ligatured under direct visual monitoring, and then connected to the arterial catheter and venous catheter respectively. With improved catheterization techniques, it is nowadays also possible to perform an isolated perfusion from outside just by puncturing the vessels, i.e. without an operation, a separation being effected between the artificial circulation and the systemic circulation.

In "Double-balloon catheter for isolated liver perfusion: an experimental study. *Cardiovasc. Intervent. Radiol.* 2001; 24: 191-193, Cwikiel et al. report on the isolated perfusion of a pig liver with four catheters. The catheters used sealed off the vessels, in which they lay, with the aid of a balloon fixed to them.

The artificial circulation in the target area can thus be separated from the systemic circulation in the rest of the human or animal body surgically, with the aid of catheters, or alternatively by ligaturing, etc.

Particularly when the isolated perfusion involves powerful but toxic medicaments, care must be taken to ensure that the isolated artificial circulation functions in isolation from the rest of the systemic circulation and that leakage of medicaments into the blood circulation is avoided, in order to ensure that the administered medicaments cannot affect the rest of the body.

However, it is often impossible to completely prevent atypical vessel courses or exits, venous plexuses or lymph tracts either surgically or by catheterization, with the result that there may be continuous exchange of blood between the artificial circulation and the blood circulation of the body.

In order to minimize this risk of leakage, a pressure drop is avoided on the venous side between the two circulations. If the pressure in the isolated artificial circulation is too low, blood flows from the systemic circulation into the treated target area, so that the blood volume circulating in the artificial circulation increases. However, the reverse scenario is of greater disadvantage, that is to say when the pressure in the artificial circulation is too high. Then, blood which contains the administered medicaments is forced into the blood circulation of the rest of the body.

It will be evident from the above that, in the context of isolated perfusion, reliable control of leakage is extremely important. In addition to guaranteeing a constant system volume on the side of the artificial circulation, leakage control has hitherto been done with the aid of radioactive substances. In "Quantitative radionuclide leakage control during isolated limb perfusion", *Nuklearmedizin* 1994; 33: 248-253, Sprenger et al. describe a twin indicator technique which uses albumin labeled with two different isotopes. The first albumin preparation is delivered to the blood circulation of the body, in order to monitor the position of the measurement probe over the heart. Slipping of the measurement probe causes a change in the signal from the measurement probe. The second albumin preparation is divided in a defined ratio between the artificial circulation and the blood circulation of the body (hereinafter also called the systemic circulation). As long as the measurement probe over the heart records a constant ratio between the first and second albumin preparations, the artificial circulation is reliably isolated from the systemic circulation. If the ratio changes, this points to a leakage.

If a leakage which has been detected in this way cannot be rectified by changing the pressure ratios, the isolated perfusion is discontinued and administration of the medicament is stopped or is not even started.

A disadvantage of the twin indicator technique, apart from the patient's exposure to radiation, is the particular effort associated with using radioactive material, in particular the requirements placed on personnel, structural measures, handling of radioactive waste, etc. Moreover, leakage via the lymph flow cannot be detected when using labeled albumin.

A further disadvantage of the twin indicator technique lies in the associated high costs arising from the expenditure in terms of technology and equipment, the personnel requirements, and the structural measures prescribed by law.

However, since isolated perfusion by catheterization can, apart from leakage control, be carried out without difficulty even in small clinics, there is a need for a simpler method of leakage control and for corresponding devices for carrying out the method.

SUMMARY OF THE INVENTION

Against this background, an object underlying the present invention is to make available a method and a device for leakage control in isolated perfusion, where the abovementioned disadvantages are avoided, so that the leakage control can be carried out economically and in a simple manner.

In the device mentioned at the outset, this object is achieved, according to the invention, by first means for feeding an analysis gas into the artificial circulation and second means for monitoring whether a blood exchange takes place between the artificial circulation and the systemic circulation, in particular whether the analysis gas passes from the artificial circulation into the systemic circulation.

The object underlying the invention is solved completely in this way.

The inventors of the present application have in fact found that reliable control of leakage is also made possible using an analysis gas which is fed into the artificial circulation. The analysis gas spreads through the perfused target area, which is accordingly saturated. However, in the rest of the body, the analysis gas is only detectable if the artificial circulation "breaks through" or leaks into the systemic circulation.

With this method, it is therefore principally possible to detect whether blood from the artificial circulation passes into the systemic circulation, which is also the important point to be checked in leakage control. However, if blood passes from the systemic circulation into the artificial circulation, this can also be detected by the fact that further analysis gas is needed to saturate this additional blood too.

Against this background, a further object of the present invention is a method in which an artificial circulation is established and maintained in a target area of a human or animal body and is isolated from the systemic circulation, and in which an analysis gas is fed into the artificial circulation and monitored to determine whether blood exchange takes place between the artificial circulation and the systemic circulation, in particular whether the analysis gas passes from the artificial circulation into the systemic circulation.

In general, the device according to the invention for isolated perfusion has, in the first means, an oxygenator for supplying the target area with oxygen and for keeping the carbon dioxide level constant. In this case, it is technically particularly easy to introduce the analysis gas into the artificial circulation since the oxygenator has, in addition to the oxygen delivery line, also an analysis gas delivery line into which the analysis gas can be introduced when the device according to the invention for isolated perfusion is connected to the human or animal body.

The analysis gas is admixed to the air stream within or upstream of the oxygenator and equilibrates with the blood, whereupon it spreads through the perfused target area. When the target area is saturated, then there is only a very small net uptake of analysis gas by the blood in the oxygenator in order to compensate for losses resulting from diffusion through the skin or through uptake by tissue with low circulation, such as fat, cartilage, and tendons.

A leakage between the artificial circulation and the systemic circulation can now be detected with the aid of a gas sensor for the analysis gas, so that, in a preferred embodiment of the device according to the invention, the second means comprise at least one gas sensor for the analysis gas.

This gas sensor can now be arranged either in a respiratory mask for the air exhaled from the body, or in the artificial circulation, or in the air outlet line from the oxygenator. According to the invention, the content of analysis gas is therefore measured either in the air exhaled from the body or in the artificial circulation, or in the air outlet line from the oxygenator.

The inventors of the present invention have in fact found that, with a gas sensor arranged in a respiratory mask for the analysis gas, it is possible, even with very slight leakage of blood from the artificial circulation into the systemic circulation, to detect the analysis gas in the exhaled air very quickly after the onset of the leakage. In this case, the gas sensor can be arranged in a ventilation mask which, in isolated perfusion, is in many cases needed anyway to anaesthetize the body.

In this case, the device according to the invention therefore comprises a pump arrangement, at least one venous catheter and at least one arterial catheter, an oxygenator, and the gas sensor arranged in a respiratory mask or introduced into an existing respiratory mask.

With the device according to the invention and with the method according to the invention, very simple isolated perfusion and leakage control is possible, and surgical interventions are no longer absolutely necessary to reliably separate the artificial circulation. By measuring the analysis gas in the exhaled air, it is in fact possible, for example, to set the pressure ratios in the artificial circulation in such a way that no leakage occurs. In addition, leakage stopping can be assisted by ligaturing, balloon catheterization, etc.

If the gas sensor is arranged in the artificial circulation, then its measurement signals can be used to monitor how the analysis gas reaches equilibrium in the artificial circulation. As soon as this is reached, only a very slight further net uptake of the analysis gas is necessary. However, if blood exchange takes place between the artificial circulation and the systemic circulation, a greater amount of analysis gas is needed for the additional equilibration, which is detected with the gas sensor arranged in the artificial circulation.

A device according to the invention thus comprises, in this embodiment, the pump arrangement, at least one arterial catheter, and at least one venous catheter, an oxygenator, and a gas sensor which is connected to the oxygenator on the side of the artificial circulation. In other words, the gas sensor is situated between the oxygenator and one of the catheters used.

In this device and in the associated method, it is advantageous that, in order to establish the artificial circulation and to monitor the latter, the catheters simply have to be connected to veins and arteries of the target area and, if appropriate, corresponding external measures have to be taken for further separation, so that the leakage monitoring itself is so to speak concomitant. It is therefore not necessary to perform any manipulations on the patient's respiratory mask.

This method is also particularly advantageous when the isolated perfusion is being performed on an animal body, for example domestic pets or zoo animals, where application of a respiratory mask can be problematic. In human patients too, advantages are afforded, since it is not necessary to perform ventilation or to reliably collect the exhaled air from spontaneously ventilating patients.

In another embodiment, the gas sensor is arranged in the air outlet line of the oxygenator, in which case a further gas sensor can preferably be arranged in the analysis gas delivery line.

In this case, a device according to the invention therefore once again comprises the pump arrangement, the venous and arterial catheters, and the oxygenator, and a gas sensor now connected to the air outlet line of the oxygenator. A further gas sensor is preferably situated on the delivery side for the analysis gas.

Using the measurement signals from the gas sensor and, if appropriate, from the further gas sensor, it is now possible to monitor the uptake of analysis gas by the artificial circulation. If, after equilibrium has been reached, an increased gas uptake is again noted, this points to a leakage.

In this arrangement, a particular advantage is that the gas sensor in the air outlet line of the oxygenator does not come into contact with the patient's blood, so that, in contrast to the oxygenator and the other tubes, it can be reused without any problem.

In order to increase comfort and safety when using the device according to the invention and to enhance employment of the method according to the invention, the measurement signals from the gas sensor and if appropriate from the further gas sensor are evaluated in a control unit which determines whether a leakage is present, and, in the presence of a leakage, switches off the artificial circulation, for which purpose it is connected to the pump arrangement.

The control unit can of course also perform other tasks in addition, for example it can be configured to inform the treating personnel that the artificial circulation is saturated with analysis gas, so that there is reliable control of leakage and the medicament can be fed into the artificial circulation.

Depending on the type of medicament delivered, it may be necessary simply to interrupt the delivery of the medicament if a leakage occurs, so that the artificial circulation can be maintained, by which means delivery to the target area is ensured.

This is practical in particular when isolated perfusion is intended to be carried out for some considerable time, in which case the control unit affords reliable monitoring of safety, especially at night, and it is not necessary to react immediately to the switching-off of the medicament delivery since the supply to the isolated target area is not compromised.

As analysis gas it is possible to use gases and other volatile substances whose concentrations can be continuously monitored in a gas mixture and which have low solubility in the blood, so that they rise and fall very rapidly and thus permit a real-time recording of a leakage. They should also have low fat solubility and thus a small virtual distribution space. Noble gases above all are suitable, although it is especially preferable to use laughing gas ($N_2O$) which is often present anyway in hospitals. Laughing gas has the advantage that it is odorless, nonexplosive, noncombustible and virtually nontoxic. For these reasons, $N_2O$ is still used today as anaesthetic gas in heart surgery.

Initial trials conducted by the inventors of the present application have revealed that the $N_2O$ sensitivity of the gas sensor, and of the optionally present further gas sensor, should be ca. 1 to 1000 ppm to ensure reliable and early detection of a leakage.

An example of a gas sensor which can be fitted in the exhaled air line, the air outlet line of the oxygenator or the delivery line for analysis gas, is the SENSIT N sensor for the NARKO-GUARD™ system from the company MSI/Drägerwerk, Lübeck. In this apparatus, the detection limit is 5 ppm $N_2O$ in air and the resolution 0.1 ppm. It is used for measurements at the work-place in connection with the checking of work safety measures and as an apparatus for leakage detection.

Against this background, the present invention also relates to the use of a gas sensor, for example an $N_2O$ sensor, in the device according to the invention or in connection with the method according to the invention.

In addition, the present invention also relates to the use of an oxygenator in the device according to the invention or in connection with the method according to the invention. The oxygenator is preferably provided with an analysis gas delivery line and also preferably with a gas sensor or an attachment for this on the air outlet side.

Finally, a further object of the invention is a kit comprising an oxygenator, an analysis gas delivery line, at least one venous catheter and at least one arterial catheter, and, if appropriate, an analysis gas sensor, and to the use of this kit in the device according to the invention or in the method according to the invention.

It shall be understood that the aforementioned features, and the features still to be mentioned below, can be used not only in the stated combination, but also in other combinations or in isolation, without departing from the scope of the present invention.

Further advantages will arise from the following description in conjunction with the attached drawing.

BRIEF DESCRIPTION OF THE DRAWING

The single FIGURE shows a diagrammatic representation of an artificial circulation which is isolated from the systemic circulation and which is maintained and monitored using the novel device.

DESCRIPTION OF PREFERRED EMBODIMENTS

In FIG. 1, reference number 10 generally designates an animal or human body in which a target area labeled 11 is separated from the rest of the body 12 by a barrier shown by lines at 13. This barrier 13 may, for example, have been created by surgical or mechanical measures.

The systemic circulation 14 with heart 15, lungs 16 and trachea 17 is also shown diagrammatically within the body 12. In the target area 11, an isolated artificial circulation 18 is indicated which is established, maintained and monitored using a device 19.

The artificial circulation 18 is separated from the systemic circulation 14 by the barrier shown at 13, but of course with the target area 11 otherwise remaining connected to the body 12. The target area 11 is for example a patient's leg which, for the purpose of thrombolytic treatment, has to be supplied for a certain time with a medicament which, for reasons of toxicity or other reasons, must not enter the systemic circulation 14. For this purpose, the barrier 13 can be effected by the veins and arteries in the target area 11 being isolated from the systemic circulation 14 surgically or by mechanical measures, such as constriction or balloon catheterization.

The device 19 comprises an arterial catheter 21 and a venous catheter 22 which is connected to a pump 23. Connected to the pump 23 there is an oxygenator 24 which is connected to the arterial catheter 21 via a tube 25. On the tube 25, a medicament feed 26 is provided via a Y-piece.

The oxygenator 24 includes a gas exchange membrane 27 which separates the artificial circulation 18 from the gas delivery line and discharge line and permits a gas equilibrium between gas side and blood side.

On the gas side, the oxygenator 24 is connected to a Y-piece 28 which is connected to a first attachment 29 for oxygen delivery and to a second attachment 31 for the delivery of an analysis gas, in this case laughing gas ($N_2O$).

The oxygenator 24 also comprises an air outlet line indicated at 33, from which the delivered oxygen and the delivered laughing gas can escape, as can also carbon dioxide released from the artificial circulation 18.

The oxygenator 24 and the second attachment 31 serving as analysis gas delivery line are means for feeding the analysis gas ($N_2O$) into the artificial circulation 18. When the analysis gas ($N_2O$) has reached equilibrium in the artificial circulation 18, there is only a very slight uptake of analysis gas in order to compensate for the losses resulting from diffusion through the skin or uptake in tissue with low circulation, as long as the the artificial circulation 18 is reliably isolated from the systemic circulation 14.

If, however, a leakage is present, that is to say blood exchange takes place between the artificial circulation 18 and the systemic circulation 14, additional gas must be delivered beyond these slight net losses.

The device 19 now has means for monitoring whether such a leakage is present.

These means comprise one or more gas sensors 34, 35, 36 and 37 which can be provided individually or in combination. The gas sensor 34 is arranged in the air exhaled from the body 12, which is preferably achieved using a respiratory mask (not shown in the FIGURE).

In the event of a leakage of analysis gas from the artificial circulation 18 into the systemic circulation 14, the analysis gas $N_2O$ can be detected in the exhaled air. The gas sensor 34 thus indicates whether analysis gas and blood from the artificial circulation 18 passes into the systemic circulation 14.

Another gas sensor 35 is arranged in the artificial circulation 18, namely between the oxygenator 24 and the arterial catheter 21. This gas sensor 35 checks the content of analysis gas in the artificial circulation 18. In the event of blood exchange between the artificial circulation 18 and the systemic circulation 14, the content of analysis gas changes beyond the change present in the equilibrated state, so that the gas sensor 35 detects a leakage.

The gas sensor 36 is connected to the air outlet line 33 of the oxygenator 24. On constant delivery of the analysis gas $N_2O$ via the second attachment 31, the gas sensor 36 emits a constant signal if the analysis gas $N_2O$ is at equilibrium in the artificial circulation 18, and only the slight net uptake for diffusion compensation changes the signal from the gas sensor 36. However, in the event of a leakage, that is to say if more analysis gas passes via the oxygenator 24 into the artificial circulation 18, the gas sensor 36 gives a reduced signal, from which a leakage can be inferred.

To take account of fluctuations in the delivery of the analysis gas $N_2O$, a further gas sensor 37 can be provided in the gas delivery line to the oxygenator 24. In this arrangement, the difference signal between the gas sensors 36 and 37 indicates the net uptake of analysis gas in the artificial circulation 18 and can likewise be used for monitoring the leakage.

The individual gas sensors 34, 35, 36, 37 are connected to associated control units 41, 42, 43 which in turn are connected to the pump 23.

The control units 41, 42, 43 record the content of the analysis gas $N_2O$ and switch the pump 23 off if a leakage is apparent from the signals from the gas sensors 34, 35, 36, 37. In this way, it is possible to ensure that, in the event of a leakage, delivered medicament does not pass into the systemic circulation 14 via the artificial circulation 18.

Instead of being connected to the pump 23, the control units 41, 42, 43 can also be connected to a medicament delivery line (not shown in the FIGURE), so that, in the event of a leakage, the artificial circulation 18 is maintained, but the delivery of the medicament through the medicament feed line 26 is prevented. This can be done, for example, by closure of a valve, indicated at 44, in the medicament feed line 26.

In particular the control units 42 and 43 can also be used in connection with establishing artificial circulation 18. If in fact these control units 42, 43 indicate that there is no change or only a very slight change in the content or uptake of the analysis gas $N_2O$, this means that the artificial circulation 18 is isolated and the target area 11 is saturated with the analysis gas $N_2O$. When this state is reached, reliable monitoring of leakage is possible, and the medicament can be fed into the artificial circulation 18.

Finally, the signals from the control units 41, 42, 43 can also be used, before feeding the medicament, to check the isolation of the artificial circulation 18. If in fact a leakage is found, this can be counteracted for example by changing the pressure on the pump 23 or by further measures at the barrier 13.

Therefore, what we claim, is:

1. A device comprising a pump arrangement, at least one venous catheter, and at least one arterial catheter, for establishing and maintaining an artificial circulation in a target area of a human or animal body, said artificial circulation being isolated from the blood circulation of the systemic body, wherein the device further comprises an oxygenator with an analysis gas delivery line into which an analysis gas can be introduced for feeding the analysis gas into said artificial circulation, and at least one gas sensor for the analysis gas for monitoring whether a blood exchange takes place between said artificial circulation and said systemic circulation and wherein the at least one gas sensor is arranged in an air outlet line of the oxygenator.

2. The device according to claim 1, further comprising at least a second gas sensor is arranged in a respiratory mask for the air exhaled from the body.

3. The device according to claim 1, further comprising at least a second gas sensor arranged in said artificial circulation.

4. The device according to claim 1, further comprising at least a second gas sensor which is arranged in the analysis gas delivery line.

5. The device according to claim 1, wherein a control unit is provided which is connected to said at least one gas sensor and to said pump arrangement, for switching off said artificial circulation in the event of a blood exchange between said artificial circulation and said systemic circulation.

6. The device according to claim 4, further comprising a control unit connected to the further gas sensor.

7. The device according to claim 1, wherein said analysis gas comprises laughing gas ($N_2O$), and said at least one gas sensor comprises an $N_2O$ sensor.

8. The device according to claim 4, wherein said analysis gas comprises laughing gas ($N_2O$), and said further gas sensor comprises an $N_2O$ sensor.

9. The device according to claim 7, wherein said at least one gas sensor has an $N_2O$ sensitivity of 1 to 1000 ppm.

10. The device according to claim 8, wherein said further gas sensor has an $N_2O$ sensitivity of 1 to 1000 ppm.

11. A device comprising a pump arrangement, at least one venous catheter, and at least one arterial catheter, for establishing and maintaining an artificial circulation in a target area of a human or animal body, said artificial circulation being isolated from the systemic blood circulation of the body, further comprising first means for feeding an analysis gas into said artificial circulation, and second means for monitoring whether said analysis gas passes from said artificial circulation into said systemic circulation, said first means comprising an oxygenator with a gas delivery line into which said analysis gas can be introduced, and said second means comprising a gas sensor arranged in an air outlet line of said oxygenator.

* * * * *

UNITED STATES PATENT AND TRADEMARK OFFICE
CERTIFICATE OF CORRECTION

PATENT NO. : 7,470,396 B2  Page 1 of 1
APPLICATION NO. : 10/670999
DATED : December 30, 2008
INVENTOR(S) : Meiser et al.

It is certified that error appears in the above-identified patent and that said Letters Patent is hereby corrected as shown below:

Title page, Item 30, please add ".7" after 102 45 772 to read --102 45 772.7--.

Signed and Sealed this

Fifteenth Day of June, 2010

David J. Kappos
*Director of the United States Patent and Trademark Office*